United States Patent [19]

Wild

[11] Patent Number: 4,923,468
[45] Date of Patent: May 8, 1990

[54] INTRAOCULAR LENS WITH FLUORESCING SUPPORT LOOPS

[76] Inventor: Victor F. Wild, 11055 Flintkote St., Bldg. 9H, San Diego, Calif. 92121

[21] Appl. No.: 365,312

[22] Filed: Jun. 13, 1989

[51] Int. Cl.⁵ .............................................. A61F 2/16
[52] U.S. Cl. ...................................................... 623/6
[58] Field of Search ..................... 623/5, 6; 351/160 R

[56] References Cited

U.S. PATENT DOCUMENTS

| | | | |
|---|---|---|---|
| 4,490,860 | 1/1985 | Rainin | 623/6 |
| 4,632,773 | 12/1986 | Neefe | 351/160 R |
| 4,676,791 | 6/1987 | LeMaster et al. | 623/6 |
| 4,687,485 | 8/1987 | Lim | 623/6 |
| 4,718,905 | 1/1988 | Freeman | 623/6 |
| 4,743,255 | 1/1986 | Bardenstein | 623/6 |

FOREIGN PATENT DOCUMENTS 2181355  4/1987  United Kingdom ................... 623/6

Primary Examiner—Randall L. Green
Assistant Examiner—David H. Willse
Attorney, Agent, or Firm—Kelly, Bauersfeld & Lowry

[57] ABSTRACT

An improved intraocular lens is provided for surgical implantation into the eye, wherein the intraocular lens includes a transparent lens body in combination with outwardly projecting support loops of a fluorescing material for enhanced visibility during implantation and in the course of postsurgical examination. In one form, the fluorescing material is integrated with monofilament support loops adapted for attachment to the transparent lens body. In another form, the fluorescing material is compounded with the support loop portions of a one-piece intraocular lens. The fluorescing material is selected to fluoresce for high visibility upon exposure to a selected illumination source, such as a relatively low power ultraviolet light.

10 Claims, 2 Drawing Sheets

INTRAOCULAR LENS WITH FLUORESCING SUPPORT LOOPS

BACKGROUND OF THE INVENTION

This invention relates generally to improvements in intraocular lenses of the type designed for implantation into the eye as a replacement for a surgically removed natural lens. More specifically, this invention relates to an improved intraocular lens including support or haptic means adapted for a high degree of visibility during implantation surgery and in the course of postsurgical examination. The improved lens of the present invention is especially suited for posterior chamber implantation.

Intraocular lenses in general are well-known for implantation into the eye as a replacement for a natural crystalline lens which has been removed surgically due to a cataract condition, injury, or the like. Such intraocular lenses are typically constructed from a transparent lens body of a selected, relatively inert and optical grade plastic material, such as polymethylmethacrylate (PMMA), having a generally disk-shaped configuration providing optical characteristics approximating a natural lens. Resilient support loops or haptics are normally provided to project outwardly from the periphery of the lens body for supporting and centering the lens body with respect to adjacent delicate eye tissue. In accordance with some intraocular lens configurations, the lens body and support loops are designed for seating in the so-called anterior chamber of the eye in front of the iris and pupil, whereas other lens designs are intended for implantation within the so-called posterior chamber behind the iris and pupil.

In accordance with recent trends in ophthalmic surgery, posterior chamber lens implantation is preferred by many surgeons largely because the lens prosthesis is positioned within the eye at or near the original position of the natural lens. Such posterior chamber implantation of an intraocular lens commonly follows so-called extracapsular extraction wherein a central anterior wall region of a transparent capsular bag or membrane containing the natural lens is surgically removed to accommodate natural lens removal, while leaving the remainder of the capsular bag intact. The intraocular lens implant is inserted through the pupil margin into the posterior chamber, desirably with the support loops seated within the periphery of the capsular bag.

Posterior implantation of an intraocular lens including the support loops constitutes a relatively difficult surgical procedure. More specifically, significant lens manipulation is required in close proximity with delicate eye tissues to pass the lens through a dilated pupil and to seat the lens in proper orientation behind the iris. Restricted visibility of the lens and/or the support loops contributes significantly to the complexity of the surgical procedure. That is, the support loops often have a relatively narrow profile which combines with visibility restrictions to make it difficult or impossible for the surgeon to visually confirm proper placement of the support loops.

Postsurgically, in some cases, problems can arise with respect to lens movement within the posterior chamber. More particularly, the intraocular lens can shift to a tilted or otherwise decentered position, resulting in visual impairment. Unfortunately, such problems are often difficult to diagnose, as a result of difficulty in seeing the precise position of the haptic support loops within the posterior chamber.

There exists, therefore, a significant need for an improved intraocular lens of the type designed particularly for posterior chamber implantation, wherein the lens includes means for facilitating and/or enhancing visibility of the haptic support loops during surgical implantation and postsurgical examination. The present invention fulfills these needs and provides further related advantages.

SUMMARY OF THE INVENTION

In accordance with the invention, an improved intraocular lens includes luminescent means such as fluorescing material for enhanced visibility during surgical implantation into the eye, and during postsurgical examination. The intraocular lens includes a transparent lens body in combination with haptic support means, wherein the fluorescing material is integrated with the support means for enhanced visibility upon exposure to a selected light source.

The transparent lens body of the improved intraocular lens is constructed from a selected, relatively inert and optical grade material such as polymethylmethacrylate (PMMA) shaped to have a generally conventional optical geometry. The lens body carries the haptic support means in the form of outwardly projecting support loops which are separately attached to or formed integrally with the lens body. These support loops provide resilient means for centering and supporting the lens at a position generally centered along a pupillary sight line when the lens is implanted into the eye. The preferred lens geometry is adapted for implantation into the posterior chamber behind the iris and pupil.

In accordance with one form of the invention, the haptic support means are formed as monofilament haptic support loops adapted for separate attachment to a transparent lens body. The fluorescing material such as fluorescein is compounded with the loop as an integral part of a monofilament core cladding as desired. In an alternative form of the invention, the fluorescing material can be integrally compounded within an annular outer sheath surrounding a transparent central region of a lens blank. The lens blank can be machined or otherwise appropriately processed to form the intraocular lens having the haptic support means formed from the annular outer sheath to project outwardly from a transparent central lens body.

The improved intraocular lens may be surgically implanted under selected lighting conditions, such as a relatively low power ultraviolet light, resulting in fluorescing of the fluorescent material used with the haptic support means. The support means is thus highly visible during the implantation procedure to facilitate proper placement by the surgeon. Moreover, during postsurgical examination, similar lighting conditions can be used for relatively easy visibility and accurate location of the haptic support means within the eye of the patient.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
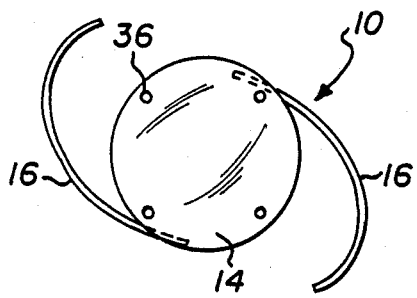
FIG. 1 is a front elevational view of an intraocular lens including fluorescing support loops, embodying the novel features of the invention.
Figure 2:
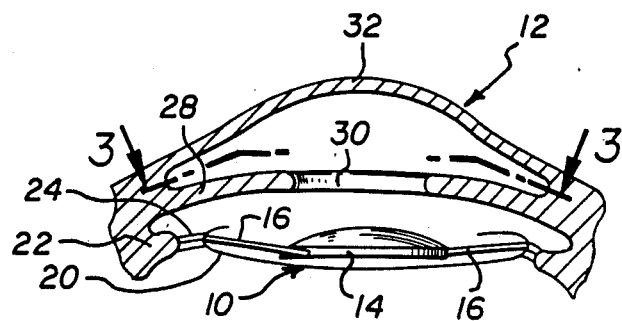
FIG. 2 is a somewhat diagrammatic view illustrating posterior chamber implantation of the intraocular lens shown in FIG. 1.
Figure 3:
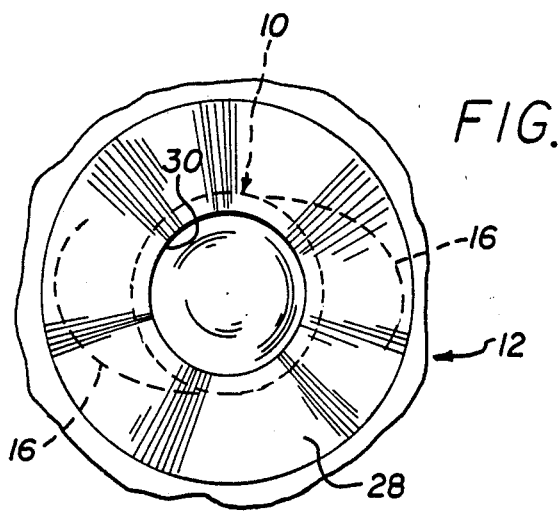
FIG. 3 is an enlarged sectional view taken generally on the line 3—3 of FIG. 2.

As shown in the exemplary drawings, an intraocular lens referred to generally in FIGS. 1-3 by the reference numeral 10 is provided for surgical implantation into an eye 12 of a patient. The intraocular lens 10 includes a transparent lens body 14 in combination with outwardly projecting support loops 16 for resiliently supporting and centering the lens body 14 within the eye. In accordance with the invention, the support loops 16 are luminescent for enhanced visibility during surgical implantation and during postsurgical examination.

The improved intraocular lens 10 of the present invention is designed for implantation into the eye following surgical removal of the natural lens (not shown). More particularly, the natural crystalline lens of the eye is encapsulated within a transparent membrane referred to commonly as the capsular bag 20 supported from the ciliary muscle 22 by suspensory ligaments or zonules 24 within a shallow chamber posteriorly of the iris 28 and the pupil opening 30 formed by the iris. Light passing through the transparent cornea 32 at the front of the eye passes further through the pupil 30 and is normally focused by the natural lens upon the retina (also not shown) at the rear of the eyeball. However, in the event the natural lens becomes clouded or otherwise experiences impaired transparency, for example, due to a cataract condition, injury, or the like, the natural lens can be removed surgically and replaced by an intraocular lens implant of the type corresponding with the invention.

In accordance with one technique preferred by many opthalmic surgeons, such technique being commonly referred to as extracapsular extraction, the natural lens of the eye is removed surgically by accessing the anterior side of the capsular bag 20 through a corneal incision (not shown) and further through the pupil 30. The anterior side of capsular bag is removed leaving the bag peripheral margin and posterior wall intact. The natural lens is thus exposed for surgical removal, with one well known surgical technique comprising ultrasonic emulsification in combination with particulate aspiration. The intraocular lens implant 10 is then passed through the incision and pupil 30 to a position seated with within the posterior chamber, and thus in a position closely corresponding with the natural lens prior to removal. The lens implant is conventionally centered and supported within the posterior chamber by two or more outwardly projecting haptics commonly in the form of the curved resilient support loops 16 which engage a peripheral region of the posterior chamber. In most instances, it is desirable for the support loops to engage the periphery of the capsular bag 20, thereby avoiding direct contact with the more sensitive ciliary sulcus region disposed forwardly of the bag 20 and the ciliary muscle 22.

The illustrative intraocular lens 10 shown in FIGS. 1-3 has a generally conventional overall geometry to include the transparent lens body 14 in combination with the outwardly projecting and curved resilient support loops 16. The lens body 14 is constructed from an optical grade and relatively inert plastic material, with polymethylmethacrylate (PMMA) being used commonly throughout the intraocular lens industry. The lens body 14 has a generally disk shaped geometry with appropriate anterior and posterior surfaces to define a selected set of optical characteristics in accordance with individual patient requirements. Small axially open positioning holes 36 may be formed near the periphery of the lens body for registry with surgical instruments to facilitate lens manipulation during an implantation procedure.

The support loops 16 are also formed from a relatively inert or biocompatible material selected to have substantial resiliency urging the loops with a spring-like action in a radially outward direction from the periphery of the lens body. In one common form, as depicted in the illustrative drawings, the support loops have a generally C-shaped or J-shaped configuration projecting generally tangentially outwardly from generally opposed lateral points on the lens body periphery. These support loops have inboard or proximal ends anchored in any suitable manner to the lens body and protrude outwardly therefrom with mirror image curvatures to define outwardly presented curved convex support surfaces. The distal ends of the support loops are spaced from the lens body periphery to accommodate radially inward compression toward the lens body in a resilient manner functioning when implanted to center and support the lens body 14 within the capsular bag 20 in substantial alignment with the pupil 30. Moreover, as viewed in FIG. 2, these loops may be provided with an anterior component of angulation to assist in maintaining the lens body 14 posteriorly of the pupil.

In accordance with the primary aspect of the invention, the support loops 16 are designed for luminescense when subjected to a selected light source, such as a relatively low power ultraviolet light or like. The support loops are thus highly visible during implantation surgery to assist the surgeon in proper seating of the intraocular lens within the posterior chamber. Moreover, during postsurgical examination, the support loops 16 are rendered highly visible to facilitate diagnosis of visual problems.

Figure 4:
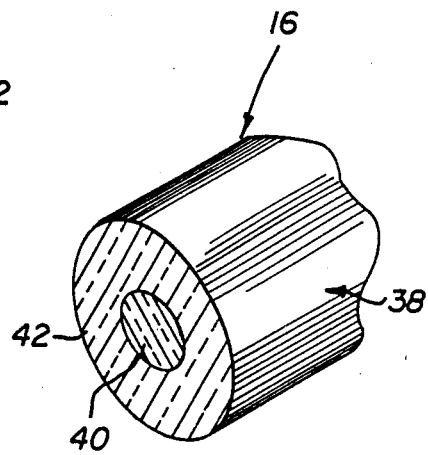
FIG. 4 is an enlarged fragmented sectional view illustrating one preferred support loop construction.

In one preferred form, the support loops 16 are constructed as a monofilament fiber 38, as viewed in FIG. 4. In this configuration, a selected fluorescing material such as fluorescein is compounded with a known support loop material, such as an acrylic fiber material or the like. The fluorescing material and acrylic fiber material are constructed as the core 40 of a support loop fiber encased within a surrounding cladding 42 of transparent support loop material, such as acrylic. The thusconstructed support loop 38 exhibits the desired combination of flexible resilient characteristics with accompanying structural integrity and biocompatibility when implanted into a patient's eye. When subjected to ultraviolet light, the fluorescing material will fluoresce to render the loop readily visible against a background of adjacent eye tissue.

Figure 5:
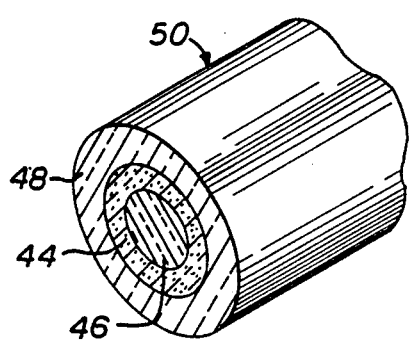
FIG. 5 is an enlarged fragmented sectional view similar to FIG. 4, but illustrating an alternative preferred support loop construction.

In an alternative form of the invention as viewed in FIG. 5, the fluorescing material can be compounded with loop material to define an intermediate sheath 44 interposed concentrically between a monofilament core 46 and outer cladding 48. In this geometry, the resultant monofilament fiber 50 again exhibits relatively high structural integrity and biocompatibility in combination with the desired resiliency for centering and supporting a lens body within the patient's eye. Once again, when subjected to ultraviolet light, the fluorescing material within the sheath 44 tends to fluoresce for high visibility during surgical implantation and/or postsurgical examination.

Figure 6:
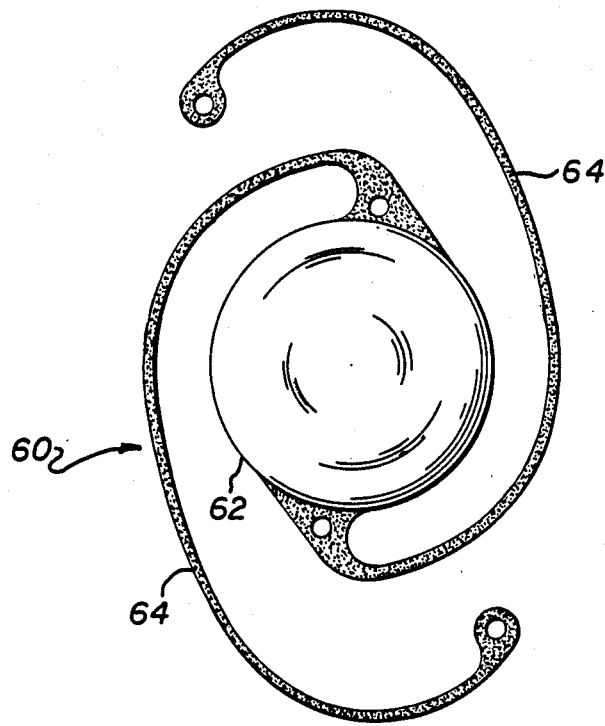
FIG. 6 is a front elevational view illustrating an alternative form of the invention.
Figure 7:
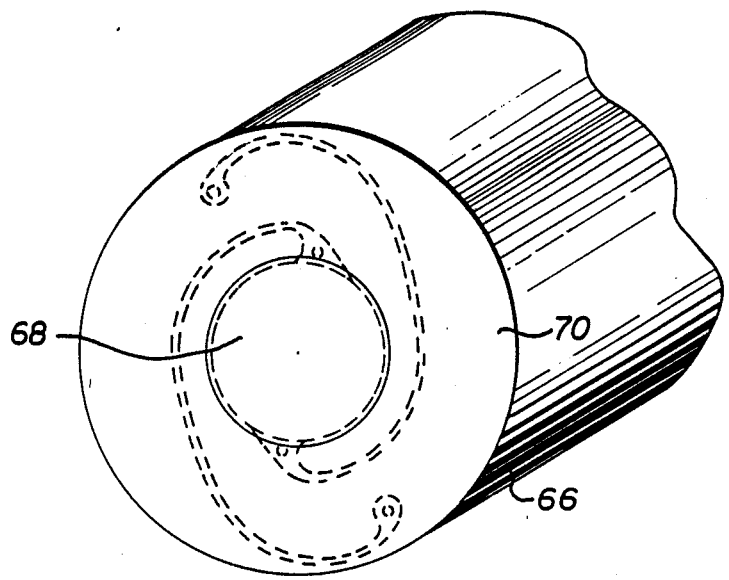
FIG. 7 is a fragmented perspective view illustrating rod stock for formation of the intraocular lens of FIG. 6.

FIGS. 6 and 7 illustrate an alternative intraocular lens 60 having a transparent lens body 62 formed integrally with outwardly projecting resilient support loops 64. The lens 60 is formed by lathe machining or the like as a one piece or integral structure from a blank cut from elongated rod stock 66 (FIG. 7) of appropriate lens material, such as PMMA or the like. However, in accordance with the invention, the rod stock 66 includes a central core 68 of transparent optical material for purposes of forming the lens body 62, wherein the core 68 is surrounded by an outer sheath 70 having the selected fluorescing material or the like compounded therein. Accordingly, when the lens 60 is formed by machining on the like, the lens body 62 is transparent to provide the desired optical qualities, and is adapted for resilient support within the eye by the support loops 64 having the fluorescing material compounded therein. Once again, the fluorescing material is adapted to fluoresce upon exposure to a selected ultraviolet light source or the like, for facilitated visibility during surgical implantation and/or postsurgical examination.

The improved intraocular lens 10 of the present invention may incorporate a variety of different fluorescing materials or other materials adapted to luminesce or fluoresce for enhanced visibility upon exposure to a selected light source. Examples include fluorescein, uranine, and other optical brightener derivatives.

A variety of further modifications and improvements to the intraocular lens 10 of the present invention will be apparent to those skilled in the art. Accordingly, no limitation on the invention is intended by way of the foregoing description or accompanying drawing, except as set forth in the appended claims.

What is claimed is:

1. An intraocular lens, comprising:
   a lens body; and
   support means for supporting said lens body within the eye of a patient, said support means including luminescent means integrated permanently therewith for luminescing upon exposure to a selected light source.

2. The intraocular lens of claim 1 wherein said luminescent means comprises a fluorescing material.

3. The intraocular lens of claim 1 wherein said support means comprises at least one monofilament fiber projecting outwardly from said lens body.

4. The intraocular lens of claim 3 wherein said fiber includes a transparent cladding formed about an inner region having said luminescent means formed integrally therewith.

5. The intraocular lens of claim 1 wherein said lens body and said support means are formed as a one-piece unit.

6. An intraocular lens, comprising:
   a lens body; and
   at least two resilient support loops secured generally to the periphery of said lens body and projecting generally outwardly herefrom to define outwardly convex support surfaces, each of said support loops being formed as a monofilament fiber having a luminescent material integrated permanently therein.

7. The intraocular lens of claim 6 wherein said luminescent material is a fluorescing material adapted to fluoresce upon exposure to a selected light source.

8. The intraocular lens of claim 6 wherein said luminescent material is formed integrally with a fiber core surrounded by a transparent fiber cladding.

9. The intraocular lens of claim 6 wherein said luminescent material is formed integrally with an intermediate sheath between a central core and a transparent cladding.

10. An intraocular lens, comprising:
    a lens body; and
    haptic support means formed integrally with and projecting generally outwardly from said lens body, said haptic support means including a luminescent material integrated permanently therewith.

* * * * *